US008551098B2

(12) United States Patent
Shimko et al.

(10) Patent No.: US 8,551,098 B2
(45) Date of Patent: Oct. 8, 2013

(54) BONE SCORING DEVICE

(75) Inventors: Daniel Andrew Shimko, Germantown, TN (US); Susan J. Drapeau, Cordova, TN (US); Kelly Brook Emerton, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 363 days.

(21) Appl. No.: 12/857,741

(22) Filed: Aug. 17, 2010

(65) Prior Publication Data

US 2012/0046663 A1    Feb. 23, 2012

(51) Int. Cl.
*A61B 17/16*    (2006.01)

(52) U.S. Cl.
USPC ............................................ 606/84; 606/185

(58) Field of Classification Search
USPC ............. 606/79–85, 131, 132, 161, 166, 167, 606/170, 172, 176–179, 184, 186, 86, 181–183; 604/22; 83/886, 887; 30/277; 234/90
See application file for complete search history.

(56) References Cited

U.S. PATENT DOCUMENTS

| 84,854 A * | 12/1868 | Brown .............................. 604/46 |
| 188,082 A * | 3/1877 | Tucker ........................... 606/183 |
| 2,124,524 A | 7/1938 | Case |
| 2,175,756 A | 10/1939 | Maury |
| 2,577,553 A | 12/1951 | White |
| 3,086,530 A * | 4/1963 | Groom .......................... 606/186 |
| 6,083,228 A | 7/2000 | Michelson |
| 6,283,971 B1 | 9/2001 | Temeles |
| 6,309,394 B1 | 10/2001 | Staehlin et al. |
| 6,530,927 B2 | 3/2003 | Staehlin et al. |
| 6,962,592 B2 | 11/2005 | Gatturna et al. |
| 7,033,359 B2 * | 4/2006 | Meller ............................ 606/80 |
| 7,604,641 B2 | 10/2009 | Tallarida et al. |
| 7,674,265 B2 | 3/2010 | Smith et al. |
| 2004/0064087 A1 * | 4/2004 | Lastovich et al. ............... 604/46 |
| 2006/0253079 A1 * | 11/2006 | McDonough et al. ........ 604/173 |
| 2009/0118735 A1 | 5/2009 | Burmeister, III et al. |
| 2010/0168749 A1 | 7/2010 | Sidebotham et al. |

OTHER PUBLICATIONS

Slap Chop, https://www.officialslapchop.com/, Jun. 11, 2010.

* cited by examiner

*Primary Examiner* — Todd Manahan
*Assistant Examiner* — Marcela I Shirsat
(74) *Attorney, Agent, or Firm* — Sorell Lenna & Schmidt LLP (57) ABSTRACT

A bone scoring device having a body, a scoring member configured to engage a bone surface and a first biasing member connected to and configured to rotate the scoring member is provided. The scoring member being axially movable between a first, non-rotatable position, such that the scoring member is engaged with the body and a second rotatable position such that the scoring member is released from engagement with the body and freely rotates. The scoring member having an abrasive surface to score the surface of the bone in which it is put in contact. A method for using the scoring device as well as a kit including the scoring device are also provided.

17 Claims, 6 Drawing Sheets

BONE SCORING DEVICE

TECHNICAL FIELD

The present disclosure generally relates to medical devices for the preparation of bone for bone graft integration, and more particularly to an automated device for creating consistent bone bed surfaces.

BACKGROUND

Any publications or references discussed herein are presented to describe the background of the invention and to provide additional detail regarding its practice. Nothing herein is to be construed as an admission that the inventors are not entitled to antedate such disclosure by virtue of prior invention.

On lay bone grafting in surgery requires preparation of the existing bone bed to encourage bone graft integration. Typical bone bed preparation involves manually scraping or perforating the existing bone bed to create bleeding bone and/or access the underlying marrow space and the resident cell populations of the existing bone. This manual bone preparation is often time consuming and can be inconsistent. Therefore, what is needed is a device that can be used to provide automated bone bed preparation that is more consistent and reproducible. The present invention provides such a device and is further described in the sections below.

SUMMARY OF THE INVENTION

These features, together with other advantages which will become subsequently apparent in light of the present description, reside in the details of construction and operation as more fully hereinafter described and claimed, reference being had to the accompanying drawings forming a part hereof, wherein like numerals refer to like parts throughout.

An object of the present invention is to provide a bone scoring device for scoring a bone bed prior to receiving a bone graft so as to more effectively allow the bone graft to adhere to the existing bone. The bone scoring device comprising a body, a scoring member configured to engage a bone surface and a first biasing member. The first biasing member is connected to and configured to rotate the scoring member. The scoring member being axially movable between a first, non-rotatable position, such that the scoring member is engaged with the body and a second rotatable position such that the scoring member is released from engagement with the body and freely rotatable. The free rotation of the scoring member scores the bone bed in which it is in contact to create bleeding bone and/or access the underlying marrow space and the resident cell populations of the existing bone.

Another objective of the present invention is to provide a bone scoring device comprising a scoring member configured to engage a bone surface, a body having an upper portion and lower portion, a shield attached to the lower portion of the body and configured to fit partially within the body and for disposal of the scoring member therein and a lid attached to the upper portion of the body. The device also comprises a plunger attached to the scoring member and positioned within the body. The plunger and scoring member being axially moveable between a first, non-rotatable position such that the scoring member is engaged with the body/shield and a second rotatable position such that the scoring member is released from engagement with the body/shield and is freely rotatable.

The scoring device of the present invention further comprises a first spring configured for rotational movement of the scoring member attached to the plunger and the lid wherein movement in a first rotational direction of the first spring loads energy in the spring in the first position and disposal of the scoring member in the second position releases the first spring to rotate the scoring member relative said body. A second spring is positioned within the body and is configured to axially move the shield from the second position to the first position relative to the scoring member. The free rotation of the scoring member of this embodiment scores the bone bed in which it is in contact to create bleeding bone and/or access the underlying marrow space and the resident cell populations of the existing bone to better attach the graft.

Another objective of the present invention is to provide a method for using the scoring device described herein. The method comprising the steps of positioning the bone scoring device of the present invention on a bone surface being prepared to receive a bone graft. Rotating the body and lid of the device to compress the first spring so as to store rotational energy therein, which may be done before or after the scoring device is firmly in place above the bone. The body and lid of the present device is compressed towards the surface of the bone so as to disengage the geared section on the shield with the geared section on the plunger and/or scoring member. With the scoring member now free to rotate, the energy stored in the first spring is released causing the scoring member to rotate.

In another embodiment, the compression of the shield within the body is translated into rotational energy stored in the first spring by rotating the scoring member by way of the geared section on said plunger and/or scoring member interacting with a geared section on said shield. As the shield is driven up into the body past the scoring member, rotational energy is stored in the first spring until the scoring member reaches a point where the geared section on the plunger disengages from the geared section on the shield. This allows the plunger and scoring member to rotate relative to the body and release the stored rotational energy in the first spring. These steps can be repeated over and over again as needed.

Still yet another objective of the present invention is to provide a kit for scoring the surface of a bone in preparation of receiving a graft. The kit comprising at least one bone scoring device of the present invention, a plurality of interchangeable replacement scoring members and at least one agent to facilitate attachment of a bone graft to the bone after scoring.

These features, together with other objects and advantages which will become subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

The exemplary embodiments illustrated in the Figures show a bone-scoring device of the present invention that can be used to create a consistent bone bed surface for receiving bone grafts. The scoring device of the present invention is designed to scrape or perforate the existing bone bed in a consistent manner in order to create bleeding bone and/or access the underlying marrow space and the resident cell populations of the existing bone. Once this is completed a bone graft placed on top of the scored bone bed can attach and heal more effectively.

The present invention may be understood more readily by reference to the following detailed description of the invention taken in connection with the accompanying figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

While the invention is described in the general context of bone grafts the device of the present invention is envisioned for all surgeries that may require bone grafting or bony defect preparation. This includes but is not limited to dental procedures, trauma related procedures, spinal procedures, orthopedic procedures, bone repair as it relates to Sports Medicine, and oncology procedures. Particular examples used in describing the device of the present invention are provided to simply assist the reader in understanding design and function of the device and in light of the specification it will be clear that the device of the present invention can be used in other bone graft procedures.

Also, as used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

The following discussion includes a description of a scoring device of the present invention, related components and exemplary methods of employing the device in accordance with the principles of the present disclosure. Alternate embodiments are also disclosed. The bone scoring device of the present invention provides a semi-automated and consistent bone scoring device for preparing a bone surface for receiving a bone graft. The bone scoring device of the present invention is an improvement over manual and inconsistent bone scoring devices since it makes the process of preparing a bone surface for bone grafting more automated and reproducible. That is, the bone scoring device of the present invention not only speeds up bone bed preparation but also improves the consistency with which bone graft material integrates with native tissues.

It is contemplated that the present disclosure may be employed with other bone or hard tissue related applications, including those associated with diagnostics and therapeutics. The system and methods of the present disclosure may also be used on animals, bone models and other non-living substrates, such as, for example, in training, testing and demonstration.

Reference will now be made in detail to the exemplary embodiments of the present disclosure, which are illustrated in the accompanying figures. Turning now to FIGS. 1-5D, there are illustrated components of the scoring device in accordance with the principles of the present disclosure.

Figure 1A:
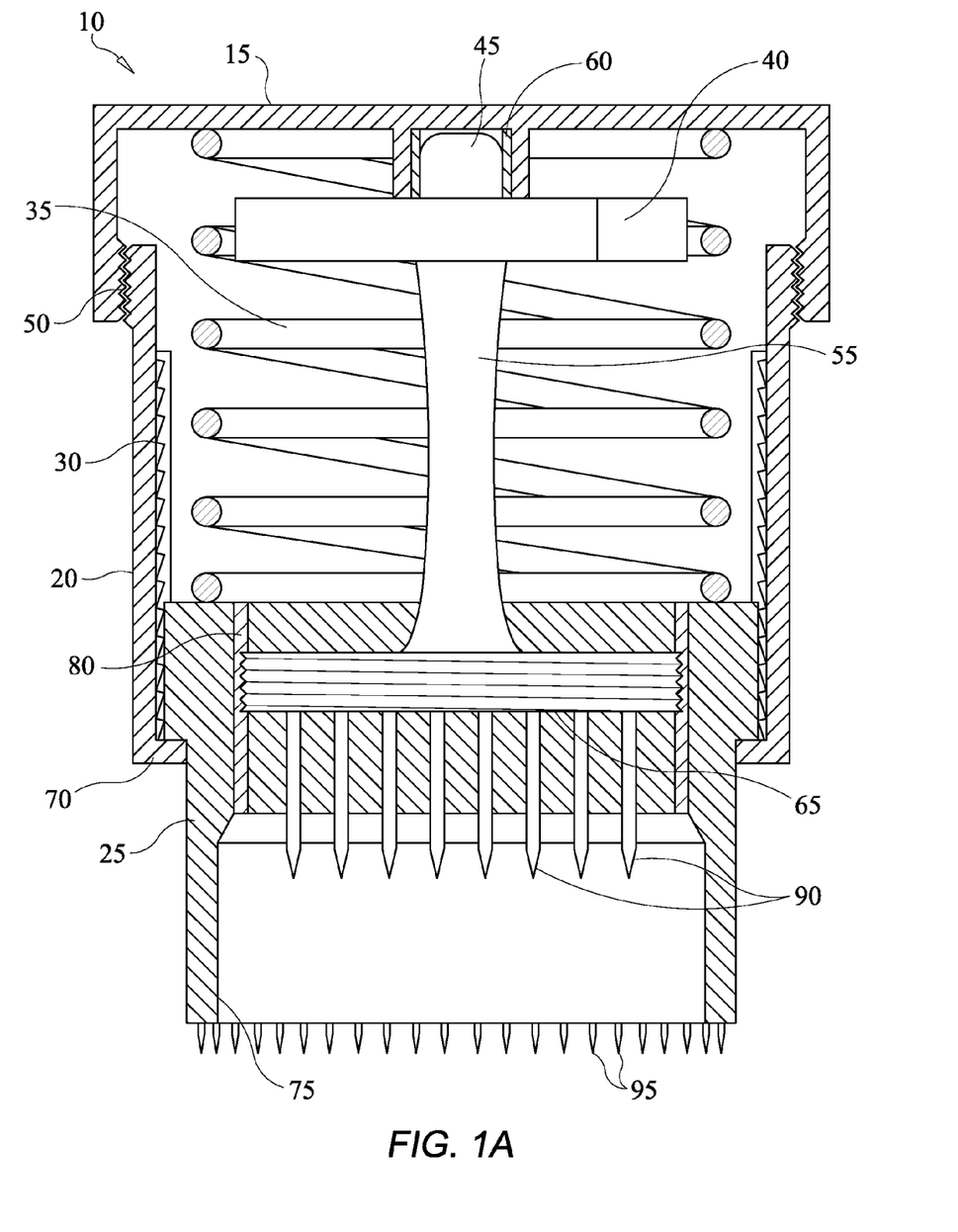
FIG. 1A is a plan view, in part cross section, of the scoring device in accordance with the principles of the present disclosure.

FIG. 1A shows a cross sectional view of the scoring device 10 of the present invention. The scoring device 10 comprises a housing having a lid 15, a body 20 and a shield 25. The lid 15 is attached to the body 20 by a fastening mechanism that is designed to attach one component to another so that these two components move as a single unit. As shown in FIG. 1A, the fastening mechanism can be mating threads 50 partly located on a portion of the inside wall of lid 15 configured to mate with a portion located the outside wall of the body 20. This arrangement allows access to the inside portion of the body 20 during manufacturing and assembly, as well as for cleaning. Once manufacturing and assembly are complete, the lid 15 is screwed to the body 20 so as to make a single unit. In an embodiment, the threads can be locking threads that are not reversible or in the alternative an adhesive can be applied to the threads during manufacturing that permanently secures the lid 15 to the body 20 after assembly.

The bone scoring device 10 also comprises a scoring member 65 configured to engage a bone surface. The scoring member 65 is attached to a plunger 55 and is positioned within the body 20 and shield 25. The scoring member 65 is equipped with a gear tooth surface 85 (or threads) that engages a geared section 80 (or mating threads) on the shield 25. Attached to the plunger 55 at one end is a scoring member 65, with the other end attached to a first biasing member 40. The first biasing member 40 is attached to the lid 15 and/or body 20 so that rotation of the lid 15 and/or the body 20 also rotates the first biasing member 40 and transfers rotational energy to the first biasing member 40. During this energy transfer event, the gear tooth surface 85 of the scoring member 65 is engaged in the geared section 80 of the shield 25, preventing rotational movement of the scoring member 65.

Figure 2:
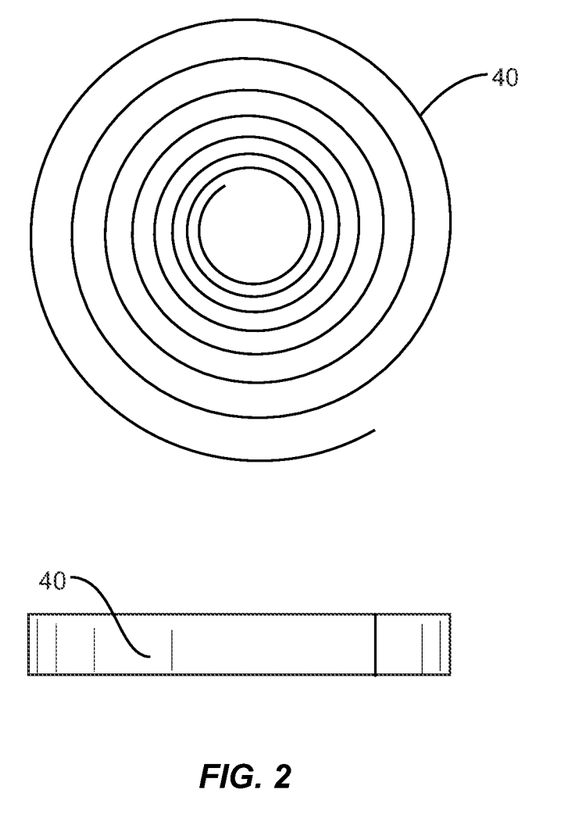
FIG. 2 is a top view and side view of the first biasing member of the scoring device in accordance with the principles of the present disclosure.

Rotation of the lid 15 and body 20 in a first rotational direction loads energy in the first biasing member 40 and rotation of the first biasing member 40 in a second direction releases energy stored in the first biasing member 40. The first biasing member 40 can be a coil, rotational spring, elastic member, or any other type of device that is capable of storing rotational energy when rotated in a first direction and releasing the stored energy by rotating in the opposite direction. A top and side view of one embodiment of the first biasing member 40 is shown in FIG. 2.

As stated herein, the first biasing member 40 serves as the connection between the lid 15 and/or body 20 and the plunger 55, which is subsequently attached to the scoring member 65. Since these elements (55 and 65) are attached to one another they function as a single unit and rotate as energy is unloaded from the first biasing member 40. The shield 25 is also axially moveable between a first position such that the scoring member 65 is engaged with the shield 25 and is non-rotatable and a second position such that the scoring member 65 is released from engagement with the shield 25 and is freely rotatable.

The shield 25 is slidably attached to a portion of the inside wall of the body 20 in a configuration that allows the shield 25 to slide towards and away from the bone surface (or into and out of the body 20). The body 20 may have a stop 70 that is configured to prevent the shield 25 from becoming separated from the body 20. This stop 70 also limits the extent in which the shield 25 extends from the body 20. The device 10 can be fitted with a ratchet system 30 (or a one-way bearing) located between the inside wall of the body 20 and the outside wall of the shield 25 so as to facilitate rotation of the body 20 relative to the shield 25 in only one direction for storing rotational energy in a first biasing member 40. The ratchet system 30 (or a one-way bearing) is designed to prevent the first biasing member 40 from releasing prematurely as rotational energy is applied to the device 10. In an exemplary embodiment, applying downward pressure on the lid 15 and the body 20 causes the shield 25 to move along the ratchet system 30 and gearing/threading mechanism 80, 85 towards the lid 15, wherein the ratchet system 30 prevents the shield 25 from retreating and motion of the shield 25 in combination with the gearing/threading mechanism 80, 85 rotates the scoring member 65 and plunger 55 which loads rotational energy in the first biasing member 40. Alternatively, a one-way bearing 30 located between the shield 25 and the body 20 may be used to allow the user to hold the shield and rotate the lid 15 and/or body 20 to load rotational energy in the first biasing member 40. Thus, the ratchet system (or a one-way bearing) 30 in combination with the gearing/threading mechanism 80, 85 restraining rotation of the scoring member 65 prevents counter rotation of the first biasing member 40 as rotational energy is supplied to it.

In an exemplary embodiment, the inner wall of the shield 25 comprises a geared tooth section 80 (or threads) that is configured to engage a gear tooth surface 85 (or threads) located on the scoring member 65. The shield 25 also includes a non-engaging surface 75 that is continuous with the geared tooth section 80 of the shield 25. In a first position, the gear tooth surface 85 of the scoring member 65 engages the geared tooth section 80 of the shield 25. Pushing down on the device 10 as shown in FIG. 3B causes shield 25 to slide up into body 25 and past the scoring member 65. In one exemplary embodiment, motion of the shield 25 past the scoring member 65 in concert with the gearing/threading mechanism 80, 85 translates the motion of the shield 25 and/or body 20 into rotation of the scoring member 65 and plunger 55, which results in stored energy in the first biasing member 40. In another exemplary embodiment, the gearing/threading mechanism 80, 85 prevents rotation of the scoring member 65, for example, the gear tooth surface 85 (or threads) located on the scoring member 65 may be protruding ridges and the geared tooth section 80 may be grooves configured to slidably mate with the protruding ridges. At the maximal position of shield 25 travel up into body 20 the plunger 55/scoring member 65 reach a position where the gearing/threading mechanism 80, 85 is no longer engaged and the scoring member 65 is free to rotate relative to the body 20. In an embodiment, the stored energy in biasing member 40 may be released by manual activation of a release mechanism attached to the first biasing member 40, allowing rotation of the scoring member 65 (e.g., see U.S. Pat. Nos. 2,175,756, 2,124,524, and 2,577,553, the entirety of each of which is incorporated by reference). In another embodiment, rotation of the scoring member 65 is achieved simply by the absence (disengagement) of rotational restraint by the gearing/threading mechanism 80, 85. For example, the movement of the scoring member 65 to the second position causes the shield 25 to impart rotational energy to the first biasing member 40 and upon disengagement of the gearing/threading mechanism 80, 85 from the plunger 55/scoring member 65, the first biasing member 40 releases the stored rotational energy therein by rotating the plunger 55/scoring member 65.

When the scoring member 65 disengages from the shield 25 and/or the rotational energy in the first biasing member 40 is released, the abrasive surface 90 of the scoring member 65 is in contact with the surface of the bone to be scored. Thus, as the rotational energy is released from the first biasing member 40, the scoring member 65 rotates and the abrasive surface 90 is scrapped along the surface of the bone. This results in scoring the bone surface to create bleeding bone and/or access the underlying marrow space and resident cell populations of the existing bone so as prepare the bone surface to receive the bone graft.

In order to facilitate the free rotation of the scoring member 65 and the plunger 55 a number of mechanisms known in the art may be used, including, but not limited to, a bearing mechanism comprising at least one ball bearing 45 disposed in a bearing track 60 attached to the lid 15. Such a configuration facilitates free rotation of the scoring member 65 relative to the body 20 and/or lid 15 upon release of stored rotational energy in the first biasing member 40. As will now be apparent in light of the present disclosure, the bearing mechanism or attachment mechanism should be such that it assures that the majority of stored energy released from the first biasing member 40 is used to rotate the scoring member 65 and is not loss to friction within the device.

Positioned within the body 20 of the device 10 is a second biasing member 35 that is configured to axially move the shield 25 from a second position, where the scoring member 65 is in contact with the bone surface, to a first position, wherein the gear tooth surface 85 of the scoring member 65 is engaged with the gear tooth section 80 on the shield 25. Once back to this starting position, the process can either be started again to further score the bone surface or the scoring device 10 can be removed.

To assure that the shield 25 does not rotate while the scoring member 65 is rotating, the bottom surface of the shield 25 that contacts the bone surface may be equipped with a plurality of grips 95. These grips 95 temporarily secure the shield 25 to the bone surface and prevent rotation of the shield 25 and/or body 20 during operation of the device 10. The grips 95 can be part of an abrasive surface or containing protruding elements to secure the shield 25 to the bone surface.

Figure 3A:
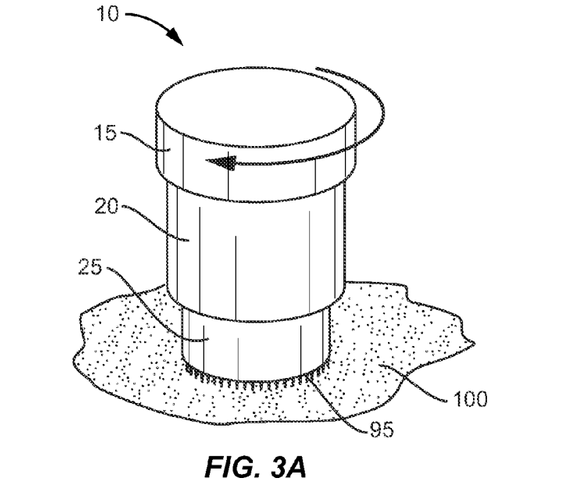
FIG. 3A is a perspective view of the scoring device of the present invention in the starting position in accordance with the principles of the present disclosure.
Figure 3B:
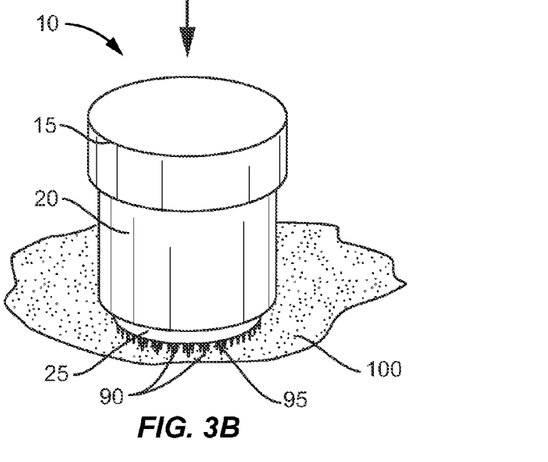
FIG. 3B is a perspective view of the scoring device of the present invention in with the scoring member in contact with the bone surface in accordance with the principles of the present disclosure.

FIG. 3A shows a perspective view of the scoring device 10 having a lid 15 attached to a body 20 that is slidable attached to the shield 25. This figure shows the scoring device in the first position. That is, the position prior to movement of the shield 25 upwards within the body 20 where the scoring member 65 is in a non-rotatable position. As discussed herein, movement of the shield 25 upwards results in the scoring member 65 (shown in FIG. 1) moving into contact with the bone surface 100. Shield 25 is shown having grips 95 that come in contact with the bone surface 100 in order to hold the shield 25 in place on the bone surface during operation. Although the grips 95 can provide scoring of the bone, their main purpose is to hold the shield 25 in place during operation of the device.

Figure 1B:
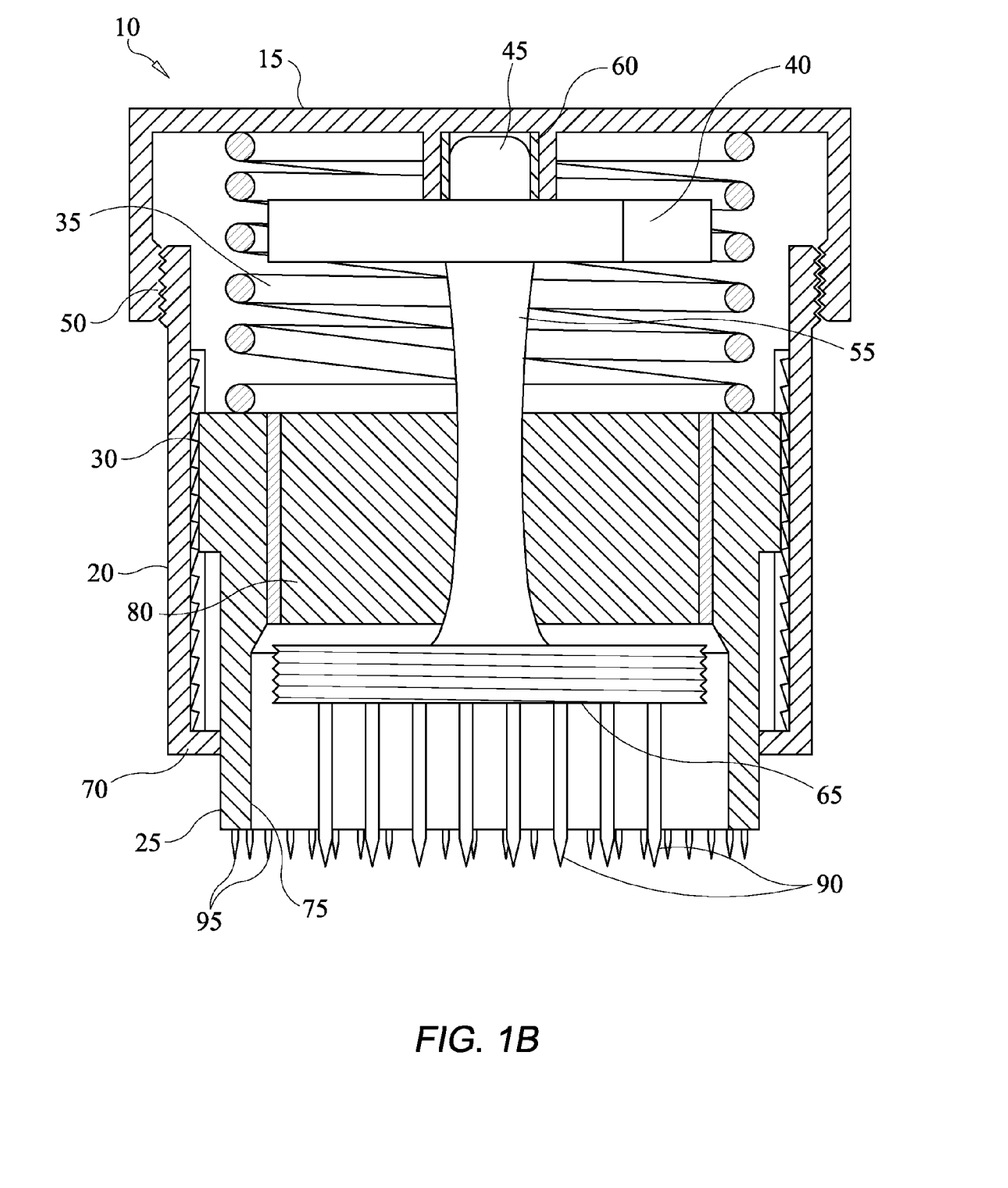
FIG. 1B is a plan view, in part cross section, of the scoring device with the scoring device in the free rotational position in accordance with the principles of the present disclosure.
Figure 3C:
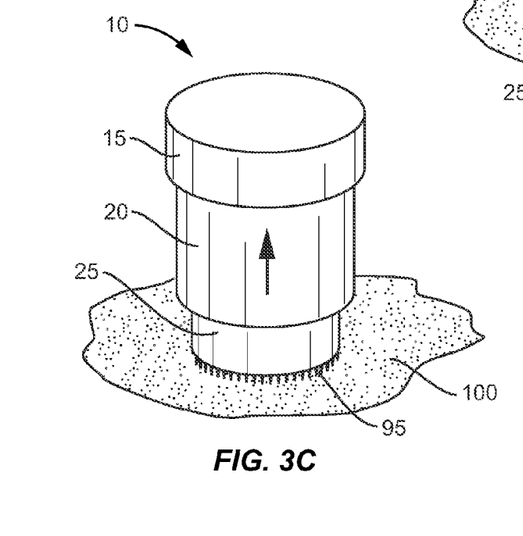
FIG. 3C is a perspective view of the scoring device of the present invention returning to the starting position in accordance with the principles of the present disclosure.

FIG. 3B shows a perspective view of the scoring device 10 of the present invention wherein the shield 25 is retracted into the body 20. As shown in FIG. 1 and discussed herein, when the shield 25 is in this position, the abrasive surface/blades 90 of the scoring member 65 are in contact with the bone surface 100. Once the rotational energy is released from the first biasing member 40, the bone scoring device 10 may be returned to the original starting position as shown in FIG. 3C. As discussed herein in connection with FIGS. 1A and 1B, this is preferably done when the scoring member 65 stops rotating and the energy stored in the second biasing member 35 is released to axially move the scoring member 65 from the second position back to the first position.

In another exemplary embodiment wherein disengagement of the gearing/threading mechanism 80, 85 allows the first biasing member 40 to spin the scoring member 65, the user may rapidly cycle through the positions shown in FIGS. 3B and 3C with a pause in the position shown in FIG. 3B sufficient to allow the scoring member 65 to come substantially to rest.

The plunger 55 with the scoring member 65 can be removably attached to the first biasing member 40 so that it can be exchanged with other plunger 55/scoring member 65 configurations having different abrasive surfaces 90. In the alternative, the device 10 of the present invention can be configured so that the scoring member 65 is removably attached to the plunger 55 so that it can be exchanged with other scoring members 65 having different abrasive surfaces 90.

Figure 4A:
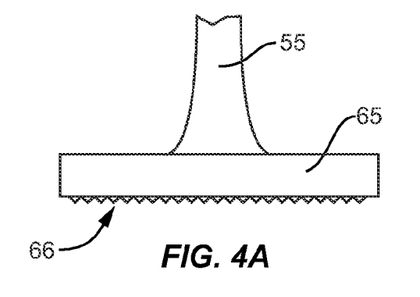
FIG. 4A is a perspective view of the scoring member having one particular abrasive surface in accordance with the principles of the present disclosure.
Figure 4B:
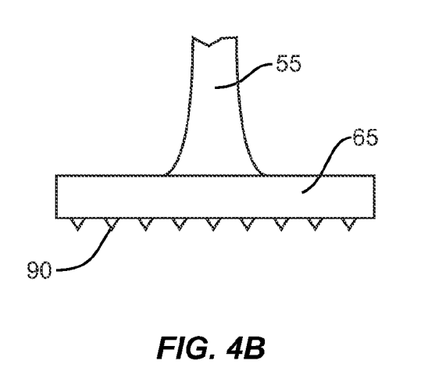
FIG. 4B is a perspective view of the scoring member having protruding cone/pyramids in accordance with the principles of the present disclosure.
Figure 4C:
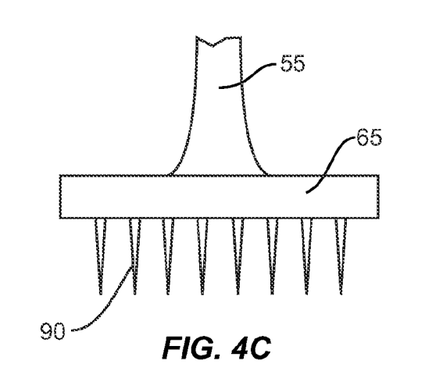
FIG. 4C is a perspective view of the scoring member having barbs in accordance with the principles of the present disclosure.
Figure 4D:
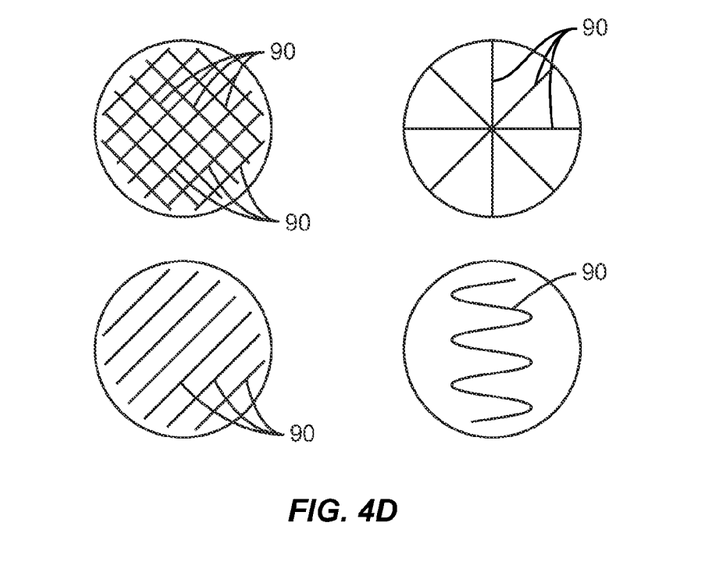
FIG. 4D is a top view a plurality of blades that can be used in scoring device in accordance with the principles of the present disclosure.

FIGS. 4A to 4D show various configurations for the abrasive surface 90 of the scoring member 65. FIG. 4A shows a side view of a scoring member 65 attached to the plunger 55 wherein the abrasive surface 90 is a roughened surface much like an emery board or sand paper. FIG. 4B shows a side view of a scoring member 65 attached to the plunger 55 wherein the abrasive surface 90 comprises a plurality of protruding cones/pyramids. FIG. 4C shows a side view of a scoring member 65 attached to the plunger 55 wherein the abrasive surface 90 comprises a plurality of barbs and/or blades. FIG. 4D shows a top view of a selection of linear blades that can be used as part of the scoring member 65 to score the surface of the bone.

Figure 5:
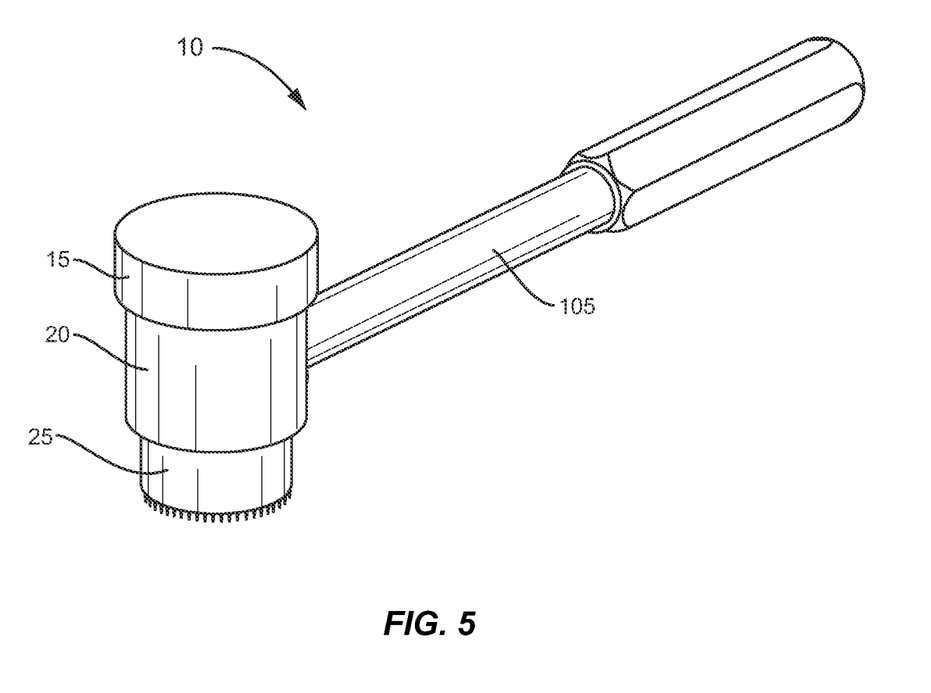
FIG. 5 is a perspective view of the scoring device of the present invention having a handle in accordance with the principles of the present disclosure.

As shown in FIG. 5, the scoring device of the present invention can be equipped with a handle 105 attached to the body 20. The handle 105 can be permanently or removably attached to the body 20 and is configured so as to facilitate handling and positioning of the scoring device of the present invention.

The components of the scoring device of the present invention may be fabricated from materials suitable for medical applications, including metals, synthetic polymers, ceramics, bone, bio-compatible materials, commercially pure titanium, titanium alloys, Grade 5 titanium, super-elastic titanium alloys, cobalt-chrome alloys, stainless steel alloys, super elastic metallic alloys (e.g. Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO$_4$ composites, ceramics and composites thereof, rigid polymers including polyphenylene, polyamide, polyimide, polyetherimide, polyethylene, polyurethanes of any durometer, epoxy and silicone, manmade materials and/or their composites. The material and shape used in manufacturing the device depends on the particular application in which the device is designed to be used. For example, since the scoring device 10 of the present invention can be used in connection with dental procedures, trauma related procedures, spinal procedures, orthopedic procedures, bone repair as it relates to Sports Medicine, and ontological procedures, the material and shape of the device may vary according the particular procedure for which the device is designed to be used.

The present invention is also directed to a method of preparing a bone bed to receive a bone graft using the scoring device 10 of the present invention. The method comprises positioning the bone scoring device 10 of the present invention on a bone surface 100 that is to be prepared for receiving a graft. Either before or after positioning the bone scoring device of the present invention on the bone, the body 20 and lid 15 is rotated relative to the shield 25 to compress the first biasing member 40 so as to store rotational energy therein. To score the bone, the lid 15 and body 20 is depressed over the shield 25 so that the geared surface 85 of the plunger 55/scoring member 65 is advanced to the non-geared section 75 on the shield 25 so that the geared surface 85 disengages from the geared section 80 allowing the plunger 55 and scoring member 65 to rotate. Once the rotation energy has been released, the shield may be returned to the extended position via the axial energy stored in the second biasing member 35 of the scoring device 10. This process can be repeated to further score the bone surface or the scoring device 10 of the present invention can be removed if the bone bed is sufficiently scored.

The present invention is also directed to a kit for scoring a bone surface in preparation for receiving a graft. The kit comprises the bone scoring device 10 of the present invention, a plurality of replacement scoring members 65 (as shown in FIGS. 4A-4D) and at least one agent designed to facilitate attachment of a bone graft to the bone surface after scoring. The agents included in the kit may include pharmacological agents, such as, for example, antibiotics, anti-inflammatory drugs including but not limited to steroids, antiviral and anti-retroviral compounds, therapeutic proteins or peptides, therapeutic nucleic acids (as naked plasmid or a component of an integrating or non-integrating gene therapy vector system), and combinations thereof.

The agents may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agents may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agents may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™ Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus). The agents may also include powdered bone to promote bone growth, bone growth factors, and other bone growth promoting agents.

In accordance with the principals of the present invention, the scoring member and the device of the present invention can be individually sterilized and packaged separately or as part of a kit. In the alternative, the entire kit can be sterilized and once it is opened, the remaining unused blades discarded. The semi-automated scoring device 10 can be disposable or re-sterilized, fitted with a new sterile scoring member 65 and used at as later time.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone scoring device comprising:
a body extending along a longitudinal axis between an upper portion and a lower portion;
a shield attached to the lower portion of the body;
a scoring member having a distal face transverse to the longitudinal axis comprising an abrasive surface configured to engage a bone surface, the abrasive surface comprising a plurality of projections extending parallel to the longitudinal axis;
a first biasing member connected to and configured to rotate said scoring member, the scoring member being axially movable between a first, non-rotatable position, such that the scoring member is engaged with the shield and a second rotatable position such that the scoring member is released from engagement with the shield and freely rotatable;
a second biasing member configured to axially move said shield from said second position to said first position, wherein the interior of the shield proximal to the body and an outer surface of the scoring member contain a gearing/threading mechanism configured to prevent free rotation of the scoring member in the first position.

2. The bone scoring device according to claim 1, wherein the body includes a plunger and wherein said scoring member is releasably connected to the plunger.

3. The bone scoring device according to claim 1, wherein the gearing/threading mechanism is configured to rotate the scoring member as the shield is moved from the first position to the second position.

4. The bone scoring device according to claim 3, wherein the gearing/threading mechanism within the shield terminates in a non-engaging surface.

5. The bone scoring device according to claim 1, wherein an outer surface of the shield includes a ratchet or one-way bearing system configured to facilitate movement of said shield relative to said body in a first rotational direction and prevent movement of the shield relative to the body in a second, opposing rotational direction.

6. The bone scoring device according to claim 1, wherein said shield includes a forward face having a rough surface configured to grip said bone surface to prevent rotation of said shield relative to said scoring member.

7. The bone scoring device according to claim 1, further comprising a bearing mechanism connected to said first biasing member to provide free rotation of said first biasing member relative to said body.

8. The bone scoring device according to claim 1, wherein the abrasive surface comprises a plurality of blades.

9. The bone scoring device according to claim 1, wherein said first biasing member is a coil spring configured to store and release energy in a rotational movement of the scoring member and said second biasing member is an axial spring configured to store and release energy in an axial movement of the shield.

10. A bone scoring device comprising:
a body extending along a longitudinal axis between an upper portion and lower portion;
a scoring member comprising a distal face transverse to the longitudinal axis having an abrasive surface configured to engage a bone surface, said abrasive surface comprising a plurality of projections extending parallel to the longitudinal axis;
a shield attached to said lower portion of said body and configured to fit partially within said body and for disposal of the scoring member therein;
a lid attached to said upper portion of said body;
a plunger releasably attached to said scoring member and positioned within said body, said scoring member being axially moveable between a first, non-rotatable position such that the scoring member is engaged with the shield and a second rotatable position such that the scoring member is released from engagement with the shield and is freely rotatable;
a first spring configured for rotational movement of the scoring member attached to said plunger and connected to said lid wherein movement of the body or lid in a first rotational direction of said first spring loads energy in said spring when the shield is in the first position; and
a second spring positioned within said body configured to axially move said scoring member from said second position to said first position.

11. The bone scoring device of claim 10, wherein said shield includes a geared tooth surface configured to engage a gear tooth surface of said scoring member, said shield further including a non-engaging surface such that in the first position the gear tooth surface of the scoring member engages the geared tooth surface of the shield, and movement of the scoring member to the second position causes the gear tooth surface of the scoring member to disengage from the geared tooth surface of the shield allowing the scoring member to rotate relative to said body and shield in response to said stored rotational energy in said first spring.

12. The bone scoring device according to claim 11, further comprising a ratchet mechanism configured to prevent premature release of stored energy in the first spring.

13. A method for scoring a bone surface comprising;
 (i) positioning said bone scoring device of claim 11 on a bone surface;
 (ii) rotating said body and lid to compress said first spring either before or after step (i) so as to store rotational energy therein;
 (iii) compressing said lid and body towards the surface of said bone so as to move said scoring member to said disengaged section on said shield so as to disengage said gear tooth surface on said scoring member from said geared section on said shield;
 (iv) releasing said stored rotational energy in said first spring and rotating said plunger and scoring member to rotate relative to said body and shield in response thereto; and
 (iv) repeating steps (i)-(iv) as needed.

14. A kit for scoring a surface of a bone comprising;
 the bone scoring device of claim 11;
 a plurality of scoring members; and
 at least one agent to facilitate attachment of a bone graft to said surface of said bone after scoring is completed.

15. The bone scoring device of claim 10, wherein said shield includes a plurality of grips on a surface closest to said bone, said grips configured to grip said bone such that said shield is prevented from rotating.

16. The bone scoring device of claim 10 wherein the abrasive surface is selected from the group consisting of protruding cones, protruding pyramids, barbs, and blades configured to scrape said bone surface.

17. The bone scoring device according to claim 10, further comprising a bearing mechanism connected to said plunger and said lid so as to provide free rotation of said scoring member relative to said body upon release of stored rotational energy in said first spring.

* * * * *